US010132727B2

(12) United States Patent
Remondini

(10) Patent No.: US 10,132,727 B2
(45) Date of Patent: Nov. 20, 2018

(54) METHOD TO MONITOR ODOROUS EMISSIONS

(71) Applicant: SACMI COOPERATIVA MECCANICI IMOLA SOCIETA' COOPERATIVA, Imola (IT)

(72) Inventor: Marco Remondini, Imola (IT)

(73) Assignee: SACMI COOPERATIVA MECCANICA IMOLA SOCIETA' COOPERATIVA, Imola (IT)

(*) Notice: Subject to any disclaimer, the term of this patent is extended or adjusted under 35 U.S.C. 154(b) by 56 days.

(21) Appl. No.: 15/034,511

(22) PCT Filed: Nov. 5, 2014

(86) PCT No.: PCT/IB2014/065826
§ 371 (c)(1),
(2) Date: May 4, 2016

(87) PCT Pub. No.: WO2015/068116
PCT Pub. Date: May 14, 2015

(65) Prior Publication Data
US 2016/0266082 A1  Sep. 15, 2016

(30) Foreign Application Priority Data

Nov. 5, 2013  (IT) ............................... BO2013A0608
Nov. 5, 2013  (IT) ............................... BO2013A0609

(51) Int. Cl.
*G01N 1/26*  (2006.01)
*G01N 35/10*  (2006.01)
(Continued)

(52) U.S. Cl.
CPC ................. *G01N 1/26* (2013.01); *G01N 1/16* (2013.01); *G01N 33/0031* (2013.01); *G01N 35/1097* (2013.01)

(58) Field of Classification Search
CPC ........ G01N 1/26; G01N 33/0031; G01N 1/16; G01N 35/1097
See application file for complete search history.

(56) References Cited

U.S. PATENT DOCUMENTS

| 4,090,392 A * | 5/1978 | Smith | ...................... G01N 1/26 |
| | | | 73/863.23 |
| 5,659,126 A * | 8/1997 | Farber | ...................... G01N 1/26 |
| | | | 422/80 |

(Continued)

FOREIGN PATENT DOCUMENTS

| DE | 101 21 033 | 10/2002 |
| WO | 2009071900 | 6/2009 |

(Continued)

OTHER PUBLICATIONS

International Search Report and Written Opinion for PCT/IB2014/065826 dated May 2, 2015.

(Continued)

*Primary Examiner* — Lisa Caputo
*Assistant Examiner* — Punam Roy
(74) *Attorney, Agent, or Firm* — Workman Nydegger

(57) ABSTRACT

Method for monitoring the odorous emissions of a plurality of zones (2, 3, 4, 5) of a given site (6); the method provides for the use of an electronic nose, and comprises a plurality of selective feeding steps, during each of which a respective sample coming from a relative zone is selectively conveyed to the electronic nose so as not to convey other gas samples coming from other zones to the electronic nose; according to some aspects of the invention, the selective feeding steps are repeated several times and the order of succession of the selective feeding steps is modified so as to control zones of particular interest more often.

17 Claims, 4 Drawing Sheets

(51) Int. Cl.
*G01N 1/16* (2006.01)
*G01N 33/00* (2006.01)

(56) References Cited

U.S. PATENT DOCUMENTS

| | | | | |
|---|---|---|---|---|
| 5,767,385 | A * | 6/1998 | Bundy | G01N 1/26 73/23.34 |
| 6,094,968 | A * | 8/2000 | Scheufler | G01N 1/26 702/77 |
| 2010/0018329 | A1 * | 1/2010 | Grziwotz | G01N 1/16 73/863.02 |

FOREIGN PATENT DOCUMENTS

| | | | | |
|---|---|---|---|---|
| WO | WO 2009068965 A1 * | 6/2009 | | G01N 33/0006 |
| WO | WO 2009071900 A1 * | 6/2009 | | G01N 33/0047 |

OTHER PUBLICATIONS

Thierry Page: "ODOWATCH Real-time Odor Emissions and Impact Monitoring Using Electronic Noses", 9 Oct. 29, 2010 (Oct. 29, 2010), XP055095575, Retrieved from the Internet: URL:http://www.baagmd.gov/-/media/Files/Compliance and Enforcement/Compliance Assistance/Odor Conf/OdoWatch—Real-time Odor Emissions and Impact Monitoring Using Electronic Noses. ashx?la=en [retrieved on Jan. 9, 2014] the whole document.

* cited by examiner

METHOD TO MONITOR ODOROUS EMISSIONS

This application is a U.S. Nationalization of PCT Application Number PCT/IB2014/065826, filed on Nov. 5, 2014, which claims priority to IT Patent Application No. BO2013A000608, filed on Nov. 5, 2013, and IT Patent Application No. BO2013A000609, filed on Nov. 5, 2013, the entireties of which are incorporated herein by reference.

TECHNICAL FIELD

The present invention relates to a method and a system for monitoring odorous emissions.

BACKGROUND TO THE INVENTION

The present invention can be applied in particular to the control of industrial sites, in particular landfills, treatment plants and/or biogas generating stations, to which the following description specifically refers without loss of generality.

In the fields indicated above, an instrument comprising an electronic nose which is moved to different areas of the industrial site is commonly used.

This procedure, however, has several drawbacks: the detection operations in the various areas take much time; for the detection operations, an operator, who moves around the site, is required continuously; it is not possible to detect the odour in several areas simultaneously.

Another known method is to position odour captivators (i.e. devices that periodically collect air samples) in different areas of the industrial site for given periods of time (typically one day), collect them and check their content via the use of an electronic nose.

In this way it is not possible to detect the odour pattern (i.e., for example, whether it is constant or reaches peaks) at various times of the day.

Furthermore, the methods used so far in the state of the art do not appear to allow the odour pattern to be identified and monitored in greater depth in specific areas of the site.

The patent document DE10121033 discloses a system for measuring the concentration of carbon dioxide, said system comprising a multiplexer connected to a plurality of ducts via respective vessels. In use, the gas is pumped through the ducts towards the multiplexer by a plurality of pumps, each arranged at one end of a relative duct opposite the multiplexer. This type of structure has some drawbacks, comprising the following: the system has a relatively high complexity and cost, since it requires a relatively high number of pumps; measurements of the samples from the various ducts can be distorted due to the different efficiencies of the pumps (the pumps may function in a slightly different way); any maintenance work on the pumps has to be performed in different places; and the remote pumping of the gas can entail variable and non-predictable pressure losses.

The object of the present invention is to provide a method and a system which overcome, at least partially, the drawbacks of the known art and at the same time are easy and inexpensive to produce.

SUMMARY

According to the present invention, a method and a system are provided as described in the following independent claims and, preferably, in any one of the claims depending directly or indirectly on the independent claims.

BRIEF DESCRIPTION OF THE FIGURES

The invention is described below with reference to the accompanying drawings, which illustrate non-limiting embodiment examples thereof, in which.

DETAILED DISCLOSURE

Figure 1:
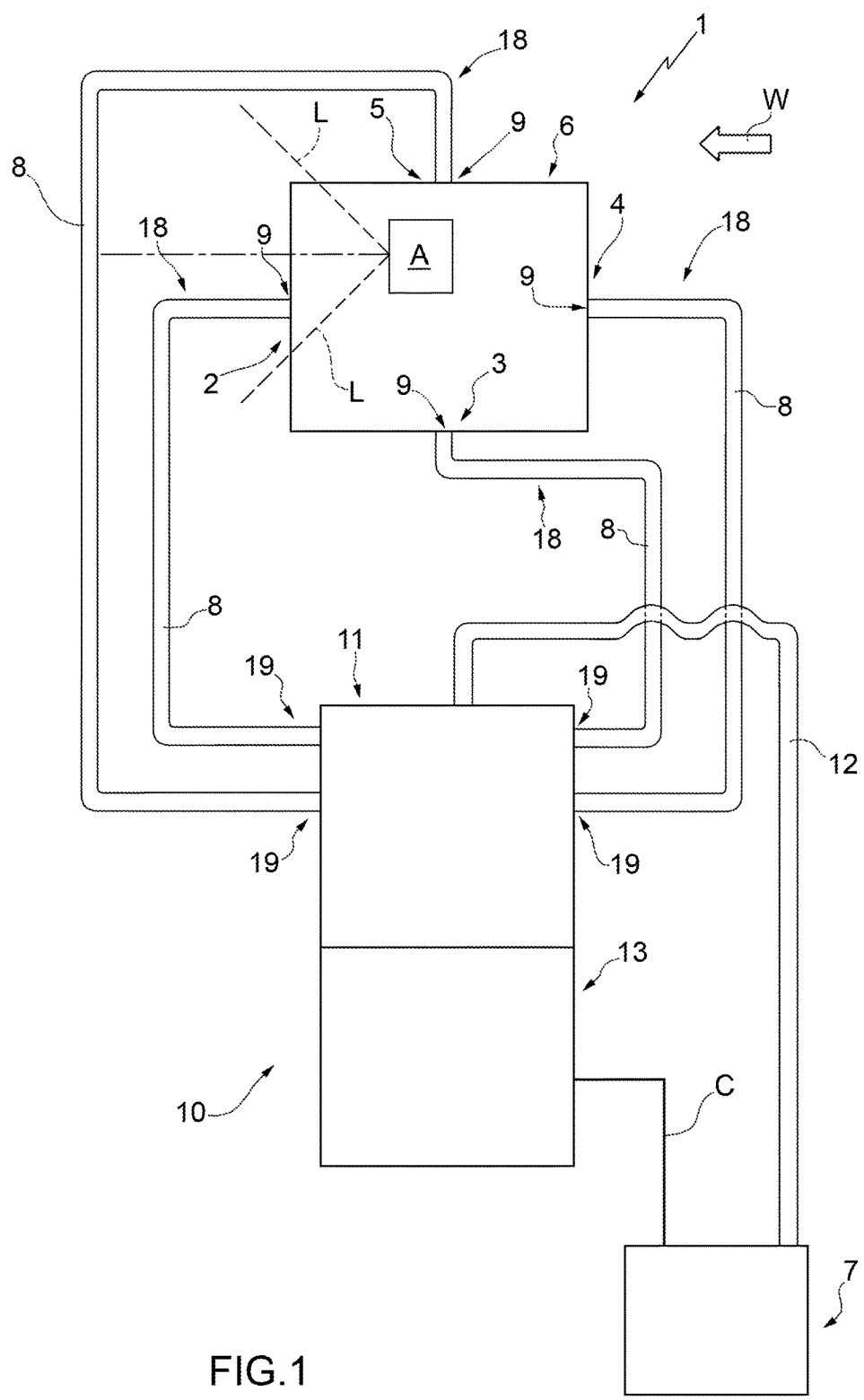
FIG. 1 schematically shows a system according to the present invention.

According to a first aspect of the present invention, in FIG. 1, the number 1 indicates as a whole a system for monitoring the odorous emissions of a plurality of (in this case four) zones 2, 3, 4 and 5 of a given site 6. In particular, the site 6 is an industrial site containing, for example, a landfill, a treatment plant and/or a biogas generating station.

The system 1 comprises a detection device 7, which is provided with an electronic nose (of per se known type and not illustrated). According to some non-limiting embodiments, the electronic nose is of the type described in the patent application PCT/IB2008/003229 (publication number WO 2009 068965) of the same holder. The electronic nose is adapted (within the limits of its capabilities, determined among other things by the type and reference data contained in it) to identify and quantify the odours contained in samples of gas (in particular air).

The system 1 furthermore comprises a plurality of (in this case four) ducts 8, each of which has a relative inlet 9 in the area of a respective one of said zones 2, 3, 4 and 5; and a gas sample collecting assembly 10, which is provided with a selector device 11 (FIG. 2) for fluidically connecting one of said ducts 8 to said electronic nose selectively so as to maintain the other duct/s 8 fluidically isolated from said electronic nose.

A fluidic connection duct 12 (FIG. 1) is also provided from the gas sample collecting assembly 10 (in particular, from the selector device 11) to the detecting device 7. A suction device (of per se known type and not illustrated) is adapted to convey portions of the samples along the connection duct 12 to the detecting device 7 (in particular, to the electronic nose). In particular, the detecting device 7 comprises the above-mentioned suction device.

Advantageously, the zones 2, 3, 4 and 5, and therefore the inlet 9, are arranged along the perimeter of the site 6.

Typically, the ducts 8 and the connection duct 12 are made of Teflon or stainless steel. These two materials are particularly suitable for this use since their capacity to absorb odours is relatively low. The use of Teflon is particularly advantageous in view of its low cost.

It should be noted that if other more absorbent materials were used, there would be the risk of altering the measurement of the odour due not only to absorption of the odour of the sample to be tested, but also due to contamination of the sample to be tested with the odour of a previous sample which is subsequently desorbed.

Figure 2:
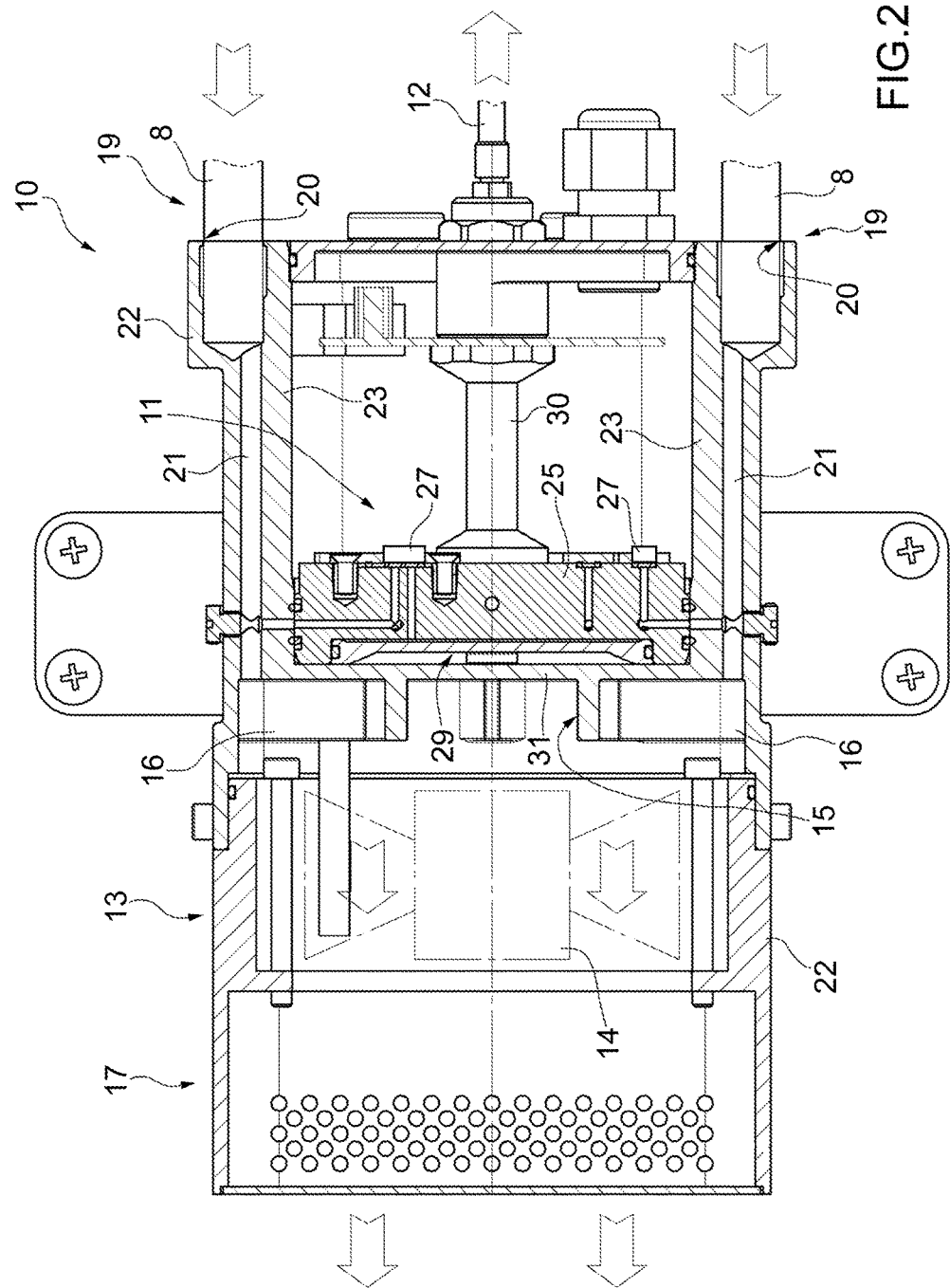
FIG. 2 is a section view of a part of the system of FIG. 1.
Figure 3:
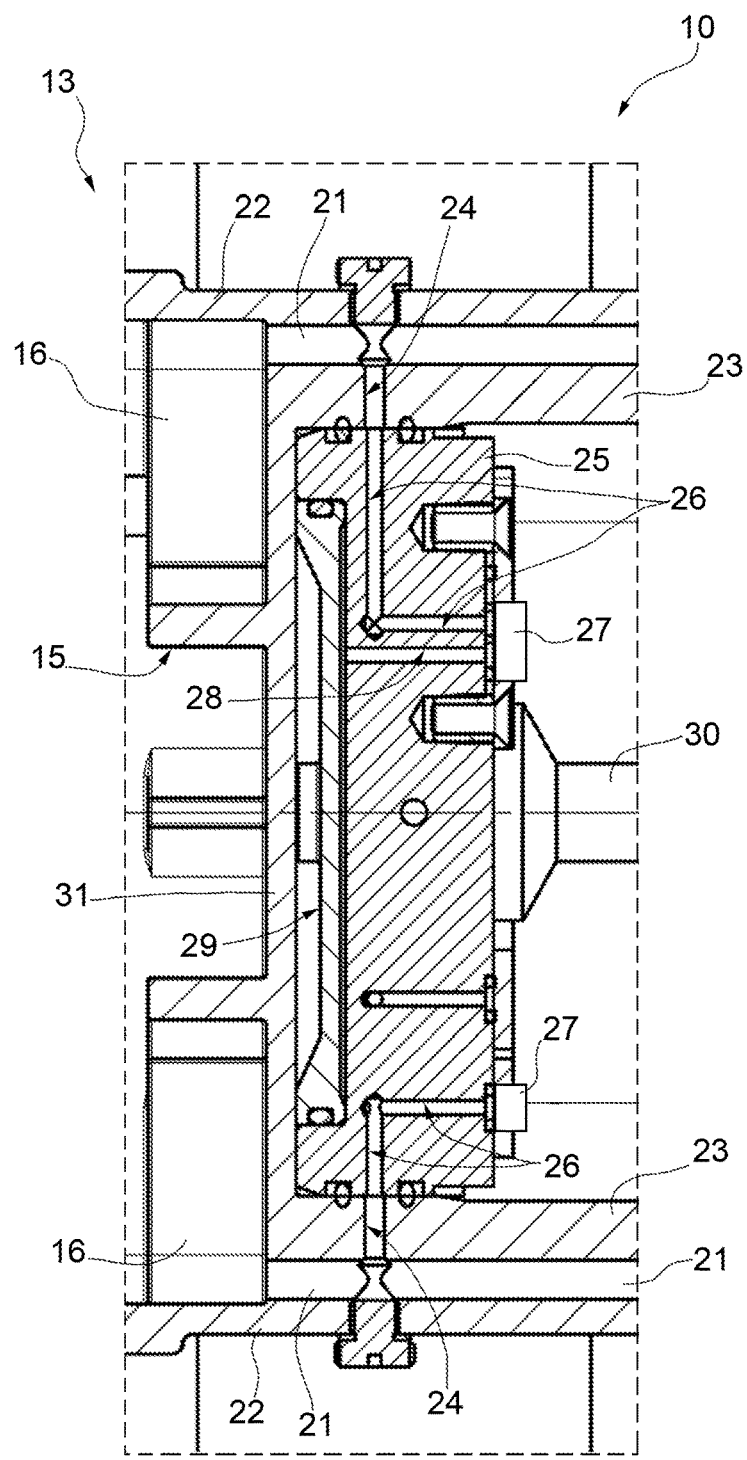
FIG. 3 shows on an enlarged scale a detail of FIG. 2.

With particular reference to FIG. 2, advantageously, the collecting assembly 10 comprises one (sole) suction unit 13 (different from the above-mentioned suction device), which is adapted to convey the gas samples along each duct 8 to the collecting assembly 10 (in particular, to the suction unit 13).

It should be noted that, on the basis of the above, it is possible to obtain transfer of the gas samples from the respective zones with relatively high speeds and substantially independently of operation of the detecting device 7 (and therefore also of the flow rate of the connection duct 12 and the respective above-mentioned suction device). Furthermore, it is also possible to exploit one single suction unit (with consequent limitation of costs) to convey all the gas samples along the ducts 8.

According to some embodiments, the suction unit 13 comprises an aspirator 14 (in particular, a suction fan; more precisely, a fan aspirator) and a suction chamber 15, which is arranged between the ducts 8 and the aspirator 14 and through which the gases from the ducts 8 are caused to pass. The suction unit 13 is adapted to discharge towards the outside the gases coming from the zones 2, 3, 4 and 5 which reach the aspirator 14.

Advantageously, in the area of the suction chamber 15 there is a stator 16, which is adapted to prevent, in the area of the suction chamber 15, the occurrence of cavitation (which reduces the operating efficiency of the aspirator 14). For this purpose, the stator 16 is provided with a plurality of fixed blades which obstruct the rotation of the air imparted by the aspirator 14.

Advantageously, the collecting assembly 10 furthermore comprises a discharging unit 17 arranged downstream of the suction unit 13 so that the gases that have reached the aspirator 14 are caused to pass through the discharging unit before being discharged to the outside. The discharging unit 17 comprises purifying means (for example activated carbon or catalysts) to retain and/or eliminate the odorous substances (by degrading them or destroying them).

According to the embodiment illustrated (see in particular FIG. 1), each inlet 9 is arranged in the area of a relative end 18 of the respective duct 8.

In particular (FIG. 2), each duct 8 has a respective further end 19 (opposite the end 18), in the area of which a relative outlet 20 is arranged. The ends 19 are coupled (in a fluid-tight manner towards the outside) to the collecting assembly 10. More specifically, each end 19 is coupled (in a fluid-tight manner towards the outside) to a respective duct 21 of the collecting assembly 10. Each duct 21 extends from the respective end 19 to the suction unit 13 (in particular to the suction chamber 15) so as to maintain in fluidic communication the relative duct 8 and the suction unit 13 (in particular the suction chamber 15).

Advantageously, the collecting assembly 10 is externally delimited by a casing 22, which encloses the selector device 11 and the suction unit 15 (and the discharging unit 17).

Typically, each duct 21 is externally delimited by the casing 22 and has a relative inner lateral wall 23 provided with a respective hole 24 which establishes fluidic communication between the duct 21 and the selector device 11.

According to the embodiment illustrated, the selector device comprises a supporting structure 25, which is arranged inside the collecting assembly 10 and along the perimeter of which the ducts 21 are positioned. In the supporting structure channels 26 are obtained, each of which extends from a respective hole 24 to a relative solenoid valve 27, and channels 28, each of which extends from the respective solenoid valve 27 to a common chamber 29. Each solenoid valve 27 is therefore adapted to allow or prevent the passage of gas from the respective channel 26 to the respective channel 28.

In particular, the chamber 29 is arranged between the supporting structure 25 and the suction chamber 15.

It should be noted that FIG. 2 shows one single channel 28 since the channel 28 associated with the channel 26 illustrated at the bottom is arranged on a different plane parallel to the plane of the sheet of FIG. 2.

The solenoid valves 27 are controlled by a control unit (not illustrated) of the detection device 7. In particular, a connection C is provided to transfer the commands from the above-mentioned control unit to the solenoid valves 27.

A further channel (not illustrated) is obtained in the supporting structure 25 to establish fluidic contact between the chamber 29 and a hollow shaft 30 coupled to the connection duct 12.

In the depicted embodiment, the chamber 29 and the suction chamber 15 are separated by a wall 31 (transverse).

Advantageously, each duct 8 is without flow regulation means. In this way the flow along the ducts 8 is regulated in practice only by the suction unit 13.

In particular, each duct 8 is without valves and further openings.

Advantageously, the suction unit 13 and the ducts 8 are such that, in use, the flow rate through each duct 8 is approximately 80 cc/min to approximately 550 cc/min. Furthermore, the suction device and the connection duct 12 are such that, in use, the flow rate through the connection duct 12 is approximately 15 cc/min to approximately 30 cc/min.

It should be noted that, advantageously, the system 1 is adapted to implement a method according to a second aspect (described below) of the present invention. According to some embodiments, the system 1 is adapted to implement a method according to a third aspect (described below) of the present invention.

In use, the gas samples are continuously conveyed from each zone 2, 3, 4 and 5 to the collecting assembly 10 along the respective ducts 8. The gas samples are then conveyed to the suction chamber 15 passing along the ducts 21. The solenoid valves 27 are all kept closed except for one so that only a portion of one of the gas samples reaches the chamber 29 and is then fed to the detecting device 7 through the connection duct 12.

To modify the origin of the gas to be tested by the detecting device, the solenoid valve 27 kept open is closed and another solenoid valve 27 is opened. After a given period, during which the detection is not recorded (in order to bleed the gas previously present in the detecting device 7 and along the connection duct 12), recording of the detections by the electronic nose is resumed.

Figure 4:
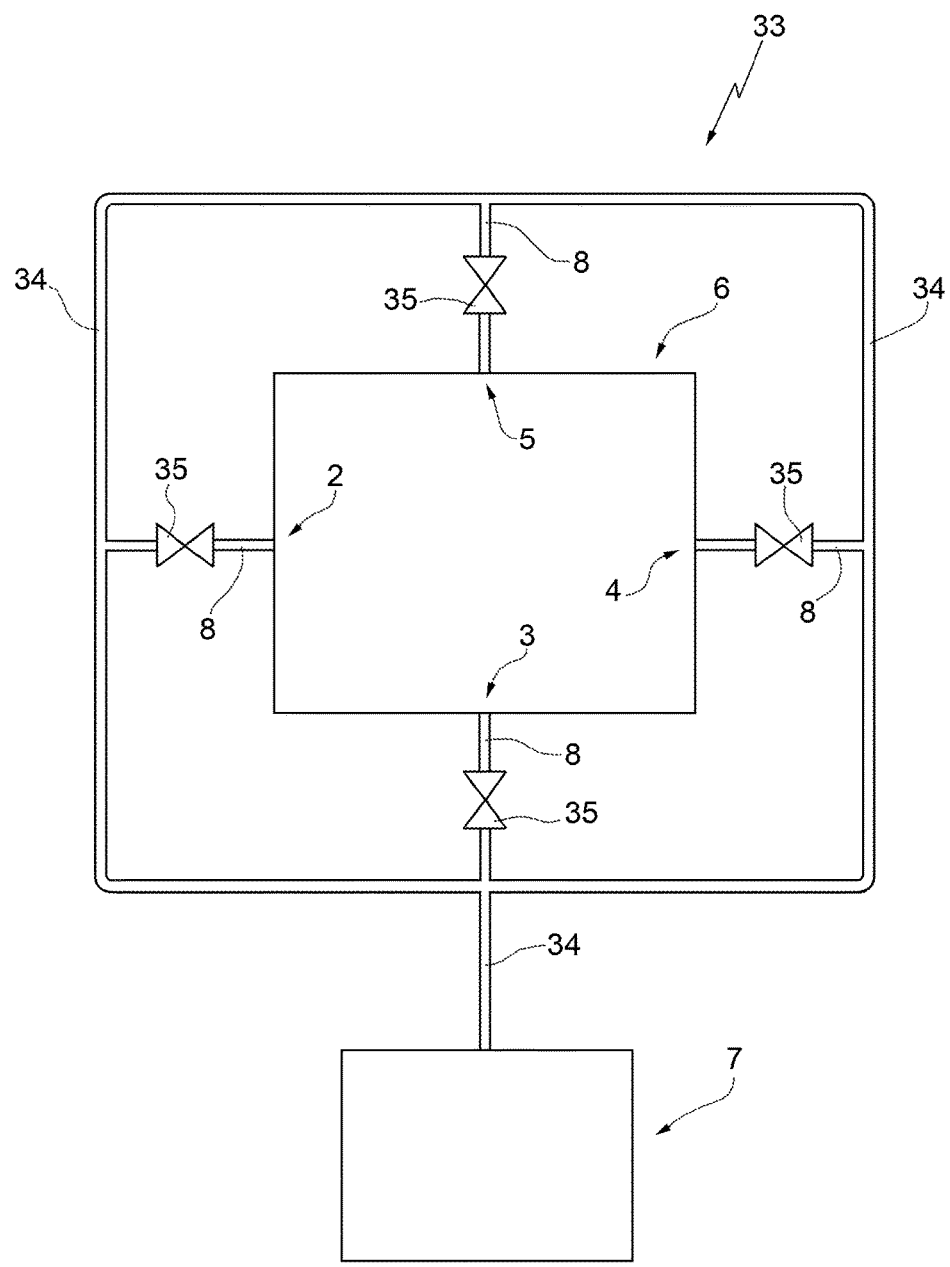
FIG. 4 schematically shows an alternative system for monitoring the odorous emissions not according to the present invention.

In FIG. 4, a monitoring system 33 alternative to system 1 is illustrated.

In this case, the ducts 8, instead of leading to a collecting assembly 10 provided with the selector device 11, are coupled with a common duct 34 which leads directly to the detection device 7. In practice the common duct 34 follows the perimeter of the site 6 and is therefore relatively long.

Each duct 8 is provided with a respective solenoid valve 35 for regulating acquisition of the sample from the different zones 2, 3, 4 and 5. In particular, in use, in order to test the odour present in zone 2, the corresponding solenoid valve is kept open and the other solenoid valves 35 are kept closed. At this point, the aspirator of the detection device 7 must be operated for a relatively long period to allow the gases coming from zone 2 to expand as far as possible along the duct 34 and reach the detection device 7 (which may be far away). To change the zone from which the samples are taken, this long and inaccurate procedure has to be repeated every time.

It is therefore evident that the system 33 has various drawbacks with respect to the system 1.

In accordance with a second aspect of the present invention, a method is provided for monitoring the odorous emissions of a plurality of (in particular, at least two) zones 2, 3, 4 and 5 of a given site 6 (in particular, an industrial site containing, for example, a landfill, a treatment plant and/or a biogas generating station). Advantageously, the zones 2, 3, 4 and 5 are arranged along the perimeter of the site 1.

The method involves the use of a monitoring system 1 comprising a detection device 7, which is provided with at least one electronic nose; a plurality of ducts 8, each of which has a relative inlet 9 in the area of a respective of said zones 2, 3, 4 and 5; a selector device 11 for fluidically connecting one of the ducts 8 to the electronic nose selectively so as to maintain the other duct/s 8 fluidically isolated from said electronic nose.

In particular, the method provides for the use of a system 1 according to the first aspect of the present invention.

The method comprises a plurality of selective feeding steps, during each of which the selector device 11 fluidically connects a selected duct 8 to said electronic nose, and at least one portion of a gas sample passing along the selected duct 8 is conveyed to the electronic nose. The other duct/s 8 is/are maintained fluidically isolated from the electronic nose.

The method furthermore comprises a plurality of testing steps, each of which is associated with a relative selective feeding step and during each of which the respective gas sample portion is tested by the electronic nose. In particular, each testing step is at least partially simultaneous with (or at least immediately subsequent to) the associated selective feeding step.

The method also comprises a plurality of source changing steps, each of which is interposed between two successive feeding steps and during each of which said selector device 11 is operated so as to change the selected duct 8 fluidically connected to said electronic nose. In other words, another of the ducts 8 comes into fluidic contact with the electronic nose while the duct 8 previously connected to the electronic nose is isolated from it.

In particular, each selective feeding step is followed by a source changing step so as to guarantee that gas sample portions coming from different zones 2, 3, 4 and 5 are tested.

Advantageously, the gas samples are conveyed through each duct substantially continuously, at least during the selective feeding, testing and source changing steps.

In this way, it is possible to obtain a forced exchange of the gas present in the ducts 8, thus surprisingly reducing the possibility of the ducts 8 absorbing odours, thereby improving the precision of the testing step.

Advantageously, the monitoring system 1 comprises a sample collecting assembly 10, which is provided with said selector device 11 and is fluidically connected to each of said ducts 8. The gas samples are conveyed substantially continuously from each zone 2, 3, 4 and 5 through each duct 8 to the collecting assembly 10.

In this way, it is possible to obtain various unexpected advantages, including: maximum reduction of odour absorption; reduction in costs (since there is one single collecting assembly for all the ducts 8); an increase in the test response speed.

In relation to this latter advantage, it should be noted that if the above procedure were not adopted, to obtain the measurement of the odour of a zone positioned far from the collecting assembly, it would be necessary to wait for the sample to travel the entire path from the above-mentioned zone to the collecting assembly 10. According to the solution proposed here, on the other hand, the sample is immediately available.

According to some embodiments, the collecting assembly comprises a suction unit 13 which conveys said samples along each duct 8 to the suction unit 13.

In this way, one single suction unit 13 can be used to convey the samples coming from all the zones, thus significantly reducing installation and running costs.

Advantageously, the selector device 11 is arranged upstream (with respect to the direction of forward movement of the gas samples) of the suction unit 13. During the selective feeding steps, the sample portions (which then undergo testing) pass through the selector device 13.

In this way, it is possible to further reduce the risk of contamination between the different samples coming from the different zones 2, 3, 4 and 5.

According to some embodiments, the monitoring system 1 comprises a connection duct 12 from the collecting assembly 10 to the detecting device 7. Movement means are also provided (different from the suction unit 13), in particular a suction device, which convey said portions along the connection duct 12 to the electronic nose during the selective feeding steps.

The feeding operations to the collecting assembly 10 and to the detecting device 7 are therefore independent of one another and can be independently controlled.

In particular, each duct 8 has a respective end 18, in the area of which the inlet 9 is arranged, and a second end 19 (opposite the end 18), in the area of which an outlet 20 is arranged. Advantageously, the second end 19 is coupled to the collecting assembly 10. The suction unit 13 comprises an aspirator 14 and a suction chamber 15, which is arranged between the outlets 20 and the aspirator 14 and through which the gases coming from the outlets 20 are caused to pass.

Advantageously, the gas samples are conveyed from each zone 2, 3, 4 and 5 through each respective duct 8 with a flow rate which is at least twice (in particular at least four times) the flow rate at which the portions are fed from the selected duct 8 to the electronic nose.

In this way, it is possible to guarantee a sufficient passage of gas through the ducts 8 (thus avoiding absorption and guaranteeing that the gas samples reach the collecting assembly in a relatively short time, among other things) and simultaneously supply gas to the detecting device 7 at the right flow rate so that the testing steps can be correctly performed.

In particular, the gas samples are conveyed from each zone 2, 3, 4 and 5 through each duct 8 (to the collecting assembly 10) at a flow rate of approximately 80 cc/min to approximately 550 cc/min. The portions are fed from the selected ducts 8 to the electronic nose at a flow rate of approximately 15 cc/min to approximately 30 cc/min.

According to a third aspect of the present invention, a method is provided for monitoring odorous emissions of a plurality of (in particular, at least two) zones 2, 3, 4 and 5 of a given site 6 (in particular, an industrial site containing, for example, a landfill, a treatment plant and/or a biogas generating station). Advantageously, the zones 2, 3, 4 and 5 are arranged along the perimeter of the site 1.

The method involves the use of a monitoring system 1 comprising a detecting device 7, which is provided with at least one electronic nose.

In particular, the method involves the use of a system 1 according to the first aspect of the present invention.

The method comprises a plurality of (in particular, at least three) selective feeding steps, during each of which a respective gas sample coming from a relative and different zone, for each feeding step, is selectively conveyed to the electronic nose so as not to convey other gas samples coming from other zones to the electronic nose.

The method also comprises a plurality of (in particular, at least three) testing steps, each of which is associated with a relative selective feeding step and during each of which the respective gas sample is tested by the electronic nose.

In particular, the method furthermore comprises at least two source changing steps, each of which is interposed between two successive selective feeding steps and during each of which the zone from which the gas sample comes is modified, said gas sample being conveyed to the electronic nose.

The method provides for the selective feeding and testing steps to be repeated several times and the order of succession of the zones 2, 3, 4 and 5 from which the gas sample comes to be modified according to one or more of the atmospheric conditions and/or the results of the test steps and/or zone of particular importance or a combination thereof.

According to some embodiments, the order of succession is modified according to one or more of the atmospheric conditions, for example the direction and/or force of the wind. In particular, the order of succession is modified so that the gas samples coming from a zone 2 downwind (FIG. 1) of an odoriferous area A (osmogenic) of the site 6 more frequently undergo the selective feeding steps and the testing steps with respect to the samples coming from the other zones 3, 4 and 5.

The zone 2 is identified as downwind referring in particular to FIG. 1, in which the arrow W indicates the wind direction.

In particular, it should be noted that the odoriferous area A is interposed between the zone 2 and from where the wind blows.

Advantageously, the zone 2 downwind is up to 45° away from the direction of the wind with respect to the odoriferous area A of the site 6. To better understand this point, in the example illustrated, the area delimited by the broken lines L is the one indicated here.

For example, when the zone 2 is downwind, the order of succession of the zones of origin of the gas sample tested could be: zone 2, zone 3, zone 2, zone 4, zone 2, zone 5, zone 2.

According to some embodiments, the order of succession of the zones 2, 3, 4 and 5, from which the sample comes, is modified when the wind speed exceeds a certain threshold.

Advantageously (therefore), the method comprises a step of detecting the direction of the wind in the area of the site 6. In some cases, the method also comprises a step of detecting the wind speed.

In some cases, the order of succession of the zones 2, 3, 4 and 5 from which the gas sample comes is modified according to the results of the testing steps.

According to some embodiments, the order of succession is modified so that the gas samples coming from a zone 2, 3, 4 and 5 in which a higher odour level is detected are subject more frequently to the selective feeding steps and testing steps with respect to the samples coming from the other zones 2, 3, 4 and 5.

If therefore, for example, the zone 2 were the zone with higher odour level, the order of succession of the zones of origin of the gas sample tested could be: zone 2, zone 3, zone 2, zone 4, zone 2, zone 5, zone 2.

Alternatively or in addition, the order of succession of the selective feeding steps is modified so that the gas samples coming from one or more zones 2, 3, 4 and 5, in which odour is detected above a given threshold, are subject with greater frequency to the selective feeding steps and testing steps with respect to the samples coming from the other zones 2, 3, 4 and 5.

Therefore if, for example, the zones 2 and 5 were the zones with odour exceeding the threshold, the order of succession of the zones of origin of the gas sample tested could be: zone 2, zone 5, zone 3, zone 2, zone 5, zone 4, zone 2, zone 5.

Alternatively or in addition, the order of succession of the selective feeding steps is modified so that the gas samples coming from one or more zones 2, 3, 4 and 5 nearer than the others to a sensitive area (for example a built-up area) are subject more frequently to the selective feeding steps and testing steps than the samples coming from the other zones 2, 3, 4 and 5.

Therefore if, for example, the zones 2 and 5 were the nearest to a built-up area, the order of succession of the zones of origin of the gas sample tested could be: zone 2, zone 5, zone 3, zone 2, zone 5, zone 4, zone 2, zone 5.

The invention claimed is:

1. A method of monitoring the odorous emissions of a plurality of zones of a given site;
the method involves the use of a monitoring system comprising a detecting device, which is provided with at least one electronic nose; a plurality of ducts, each of which has a relative inlet in the area of a respective one of said zones;
a selector device to fluidically connect one of said ducts to said electronic nose in a selective way, so as to keep the other ducts fluidically isolated from the electronic nose itself;
the method comprising:
a plurality of selective feeding steps, during each of which the selector device fluidically connects a selected duct to said electronic nose and at least a portion of a gas sample flowing through the selected duct is conveyed to the electronic nose; the other duct/s being kept fluidically isolated from the electronic nose;
a plurality of testing steps, each of which is associated with a relative selective feeding step and during each of which the respective portion of gas sample is tested by the electronic nose;
a plurality of source changing steps, each of which is interposed between two successive feeding steps and during each of which said selector device is operated so as to change the selected duct that is fluidically connected to the electronic nose;
conveying gas samples from each zone through each duct in a substantially continuous way, at least during the selective feeding steps, the testing steps and the source changing steps;
the monitoring system comprises a gas sample collecting assembly, said collecting assembly being provided with said selector device and being fluidically connected to each one of said ducts; the gas samples being conveyed in a substantially continuous way from each zone to the collecting assembly through each duct;
the collecting assembly comprises a suction unit, which conveys said samples, along each duct, to the suction unit itself; the selector device being arranged upstream of the suction unit and, during the selective feeding steps, said portions flow through the selector device, the selective feeding and testing steps being repeated and the order of succession of the zones from which the gas sample comes being modified according to a variable chosen in the group consisting of: one or more of the atmospheric conditions, the results of the testing steps, zone of particular importance or a combination thereof, wherein the monitoring system comprises a connection duct extending from the collecting assembly to the detecting device; and moving means which convey said portions, along the connection duct, to the electronic nose during the selective feeding steps.

2. A method according to claim 1, wherein each duct has a respective first end, where the relative inlet is arranged, a respective second end, where a relative outlet is arranged; the second end being coupled to the collecting assembly; said suction unit comprising an aspirator and a suction chamber, which is arranged between said outlets and said aspirator and through which the gases coming from the outlets are caused to flow.

3. A method according to claim 1, wherein the gas samples are conveyed from each zone through each respective duct with a flow rate that is at least twice, the flow rate with which the portions are fed from each selected duct to the electronic nose.

4. A method according to claim 1, wherein the gas samples are conveyed from each zone through each duct with a flow rate ranging from approximately 80 cc/min to approximately 550 cc/min; the portions are fed from each selected duct to the electronic nose with a flow rate ranging from approximately 15 cc/min to approximately 30 cc/min.

5. A method according to claim 1, wherein the order of succession of the zones from which the gas sample comes is modified according to the variable chosen in the group consisting of: one or more of the atmospheric conditions, the results of the test steps, or a combination thereof.

6. A system for monitoring the odorous emissions of a plurality of zones of a given site, to implement a method according to claim 1;

the system comprises:
a detecting device, which is provided with at least one electronic nose; a plurality of ducts, each of which has a relative inlet in the area of a respective one of said zones;
a gas sample collecting assembly, which is provided with a selector device for fluidically connecting one of said ducts to said electronic nose selectively so as to maintain the other ducts fluidically isolated from said electronic nose;
a fluidic connection duct from the selector device to the detecting device; and
movement means to convey at least portions of the gas samples along the connection duct to the electronic nose;
the gas sample collecting assembly comprising:
a suction unit which is adapted to convey said samples along each duct to said collecting assembly; each duct being without flow regulation means; each duct having a respective first end, in the area of which the relative inlet is arranged, and a respective second end, in the area of which a relative outlet is arranged; the second end being fluidically connected to the collecting assembly; said suction unit comprising an aspirator and a suction chamber, which is arranged between said outlets and said aspirator and through which the gases coming from the outlets are caused to flow, each duct being without valves and further openings, the system further comprising a discharging unit arranged downstream of the suction unit and through which, in use, the gases which have reached the suction chamber are caused to pass in order to be discharged towards the outside.

7. A system according to claim 6, wherein the discharging unit comprises purifying means to retain and/or eliminate odorous substances.

8. A method according to claim 1, and comprising a first operation phase, during which the selective feeding and testing steps are repeated following a first order of succession of the zones from which the gas sample comes; and a second operation phase, which is after the first operation phase and during which the selective feeding and testing steps are repeated following a modified order of succession of the zones from which the gas sample comes, which modified order is different from the first order; the order of succession of the zones from which the gas sample comes being modified according to the variable chosen in the group consisting of: one or more of the atmospheric conditions, the results of the testing steps, zone of particular importance or a combination thereof.

9. A method of monitoring the odorous emissions of a plurality of zones of a given site; the method involving the use of a monitoring system comprising a detecting device provided with at least one electronic nose;

the method comprising a plurality of selective feeding steps, during each of which a respective gas sample coming from a relative and different zone for each feeding step is selectively conveyed to the electronic nose so as to avoid conveying other gas samples coming from other zone/s to the electronic nose;

a plurality of testing steps, each of which is associated with a relative selective feeding step and during each of which the respective gas sample is analysed by the electronic nose;

the method providing for the selective feeding and testing steps to be repeated and the order of succession of the zones from which the gas sample comes to be modified according to a variable chosen in the group consisting of: one or more of the atmospheric conditions, the results of the testing steps, zone of particular importance or a combination thereof, wherein the order of succession is modified according to the direction and/or force of the wind.

10. A method according to claim 9, wherein the order of succession is modified according to a variable chosen in the group consisting of: direction and/or force of the wind, quantity of odour detected in each zone, proximity of the zone to sensitive areas or a combination thereof; there being at least three selective feeding steps, during each of which a respective gas sample coming from a relative different zone, for each feeding step, is selectively conveyed to the electronic nose so as to avoid conveying other gas samples coming from other areas to the electronic nose; there being at least three testing steps, each of which is associated with a relative selective feeding step and during each of which the respective gas sample is analysed by the electronic nose.

11. A method according to claim 9, wherein the order of succession is modified so that the gas samples coming from one or more zones downwind with respect to an (osmogenic) odoriferous area of the site more frequently undergo the selective feeding steps and the testing steps with respect to the samples coming from the other zones.

12. A method according to claim 11, wherein the odoriferous area is interposed between the zone downwind and the zone from where the wind blows.

13. A method according to claim 11, wherein the zone downwind is up to 45° away from the direction of the wind with respect to the odoriferous area of the site.

14. A method according to claim 9, wherein the order of succession of the selective feeding steps is modified so that the gas samples coming from one or more zones, in which a higher level of odour is detected, more frequently undergo the selective feeding steps and the testing steps with respect to the samples coming from the other zones.

15. A method according to claim 9, wherein the order of succession of the selective feeding steps is modified so that the gas samples coming from one or more zones in which odour is detected above a given threshold more frequently undergo the selective feeding steps and the testing steps with respect to the samples coming from the other zones.

16. A method according to claim 9, wherein the order of succession of the selective feeding steps is modified so that the gas samples coming from one or more zones nearer than the others to a sensitive area more frequently undergo the selective feeding steps and the testing steps with respect to the samples coming from the other areas.

17. A method according to claim 9, wherein said zones are arranged along the perimeter of the site.

\* \* \* \* \*